United States Patent
Chambers et al.

(10) Patent No.: US 10,213,126 B1
(45) Date of Patent: Feb. 26, 2019

(54) DETECTOR ARRAYS WITH ELECTRONICALLY ADJUSTABLE DETECTOR POSITIONS

(71) Applicant: Raytheon Company, Waltham, MA (US)

(72) Inventors: Matthew D. Chambers, Goleta, CA (US); John L. Vampola, Santa Barbara, CA (US); Micky Harris, Lompoc, CA (US)

(73) Assignee: Raytheon Company, Waltham, MA (US)

( * ) Notice: Subject to any disclaimer, the term of this patent is extended or adjusted under 35 U.S.C. 154(b) by 0 days.

(21) Appl. No.: 16/173,442

(22) Filed: Oct. 29, 2018

Related U.S. Application Data

(62) Division of application No. 14/711,042, filed on May 13, 2015, now Pat. No. 10,130,280.

(51) Int. Cl.
| | |
|---|---|
| *H04N 1/46* | (2006.01) |
| *G06F 3/12* | (2006.01) |
| *A61B 5/05* | (2006.01) |
| *H01L 27/148* | (2006.01) |
| *H04N 5/372* | (2011.01) |
| *H04N 5/374* | (2011.01) |
| *H04N 5/347* | (2011.01) |
| *A61B 5/00* | (2006.01) |

(52) U.S. Cl.
CPC .......... *A61B 5/05* (2013.01); *H01L 27/14856* (2013.01); *H04N 5/347* (2013.01); *H04N 5/3743* (2013.01); *H04N 5/37206* (2013.01); *A61B 5/7203* (2013.01); *A61B 2562/046* (2013.01); *A61B 2576/00* (2013.01)

(58) Field of Classification Search
CPC ... A61B 5/05; A61B 5/7203; A61B 2562/046; A61B 2576/00; H01L 27/14856; H04N 5/347; H04N 5/37206; H04N 5/3743
See application file for complete search history.

(56) References Cited

U.S. PATENT DOCUMENTS

| | | | |
|---|---|---|---|
| 5,101,108 | A | 3/1992 | Gaalema et al. |
| 8,300,276 | B2 | 10/2012 | Vampola |

(Continued)

FOREIGN PATENT DOCUMENTS

| | | |
|---|---|---|
| CN | 103918253 A | 7/2014 |
| CN | 105580352 A | 5/2016 |

OTHER PUBLICATIONS

Chinese Office Action from related Chinese Application No. CN201680017480.X dated Jul. 3, 2018.

(Continued)

*Primary Examiner* — Quang N Vo
(74) *Attorney, Agent, or Firm* — Burns & Levinson, LLP; Joseph M. Maraia

(57) ABSTRACT

A system including a detector array configured to receive electromagnetic (EM) radiation from a target object, the detector array having one or more detectors is disclosed. The system also includes a readout integrated circuit and one or more processors. The readout integrated circuit has a circuit comprising a number of detector boundary selection components, each one of the number of detector boundary selection components configured to select or adjust a detector boundary from least one of a sub-column boundary or an adjustable boundary.

8 Claims, 10 Drawing Sheets

(56) References Cited

U.S. PATENT DOCUMENTS

| | | |
|---|---|---|
| 9,253,426 B2 | 2/2016 | Mayer et al. |
| 2008/0151088 A1 | 6/2008 | Frey et al. |
| 2011/0019044 A1 | 1/2011 | Wang et al. |
| 2015/0011850 A1* | 1/2015 | Ruchti ............... A61B 5/14532 600/316 |

OTHER PUBLICATIONS

International Search Report and Written Opinion from related PCT Application No. PCT/US2016/021309 dated Jun. 2, 2016.

* cited by examiner

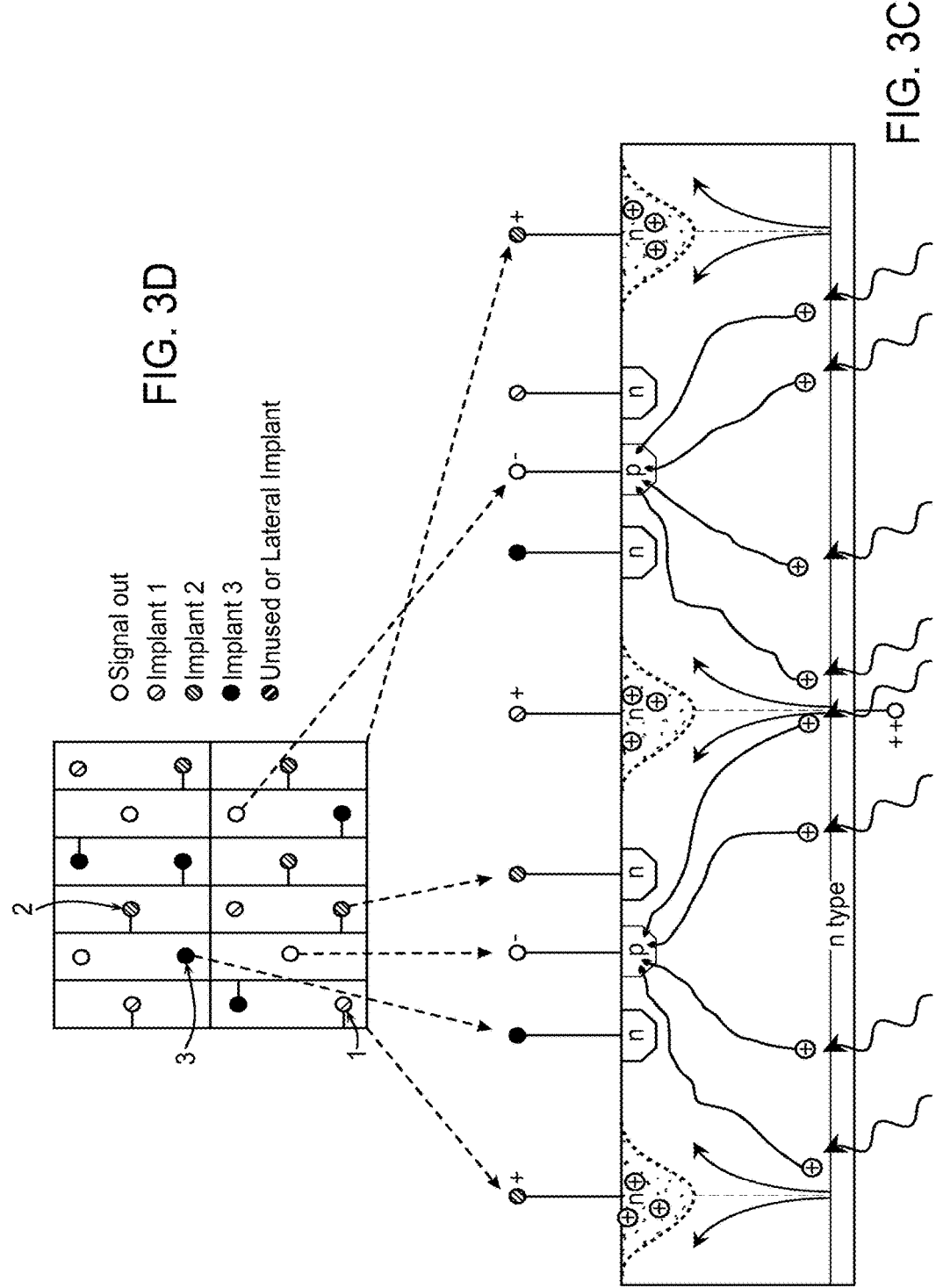

DETECTOR ARRAYS WITH ELECTRONICALLY ADJUSTABLE DETECTOR POSITIONS

CROSS-REFERENCE TO RELATED APPLICATIONS

This application is a Divisional of U.S. application Ser. No. 14/711,042, filed on May 13, 2015, entitled DETECTOR ARRAYS WITH ELECTRONICALLY ADJUSTABLE DETECTOR POSITIONS, which is incorporated by reference herein in its entirety for all purposes.

BACKGROUND

The present teachings relate to detector arrays with electronically adjustable detector positions and methods for application of the detector arrays with electronically adjustable detector positions. The applications include compensating for misalignment in an image scanner, and synthetic improvement of image resolution.

There are a number of possible applications for detector arrays, which receive electromagnetic radiation from a target object, where adjustable detector positions would be desirable. One of those applications is compensation for misalignment in image scanners. Another application is the synthetic improvement of spatial resolution.

A time delay and integration (TDI) image scanner accumulates multiple exposures of the same object as the object moves relative to the scanner. When a scanning imager, or elements therein, sweep through a scan that is off-nadir the image tracks across the focal plane in an arc and image elements that begin in one scan column may end in a different scan column. If uncorrected, this smears the image across multiple columns and degrades modulation transfer function (MTF). Digital corrections can account for the approximate column location of each image element, as an integer, through the course of a scan, reducing smear to a half-pixel, but cannot compensate for the splitting of image elements across two detector pixels as they track from one column into the next.

"Off-nadir" scan smearing can be corrected by accounting for the tracking of the image across columns of a multi-row scanner during a scan. This can be done digitally; for instance, in the case of time-delayed integration (TDI) scanners, one might add rows 1-10 of column 1 to a single integrated image pixel, followed by rows 11-20 of column 2. This approach can reduce smear to a half-pixel. Correction can also be done by dynamic aggregation of detector pixels of a smaller size than corresponding to the final image pixel (in the cross-scan dimension) into single image pixels. This approach, again, can reduce smear to, at best, a half-pixel. Since for both these cases, the amount of smear is relative to the detector pixel size, it can be reduced by reducing the cross scan pixel dimension. However, this requires additional pixel unit cells. For hybrid sensors, the number, size, and density of detector-to-readout integrated circuit (ROIC) interconnects therefore present additional constraints in terms of spacing and alignment tolerances. The addition of pixel unit cells is also not always desirable since it requires compression of more per-pixel circuitry into the same space for a given detector size, and it can increase the overall noise of the signal collected by the detector by reason of multiplying constant per-pixel noise sources.

Similar needs for correction arise from other factors that can displace an image from the nominal column in which it would normally be expected, including but not limited to: mechanical jitter; optical aberration in the system; optical aberration caused by environments interposed between the target object and the imaging system.

There is a need for systems and methods that can reduce misalignment or smear to better than half a pixel.

There is a need in a number of applications, such as, but not limited to, improving image resolution, for a system and method for adjusting detector position and size.

BRIEF SUMMARY

A system and method for adjusting detector position and size in detector arrays is disclosed herein below.

In one or more embodiments, the system of these teachings includes a detector array configured to receive electromagnetic (EM) radiation from a target object, the detector array having one or more detectors. The system also includes a readout integrated circuit and one or more processors, any of which may be contained within the readout circuit. In the detector array, the detectors are organized into a plurality of segments, each segment having one or more rows of the detectors substantially perpendicular to a designed scan axis, each segment having a one or more columns of detecting components substantially parallel to the designed scan axis, each of the one or more columns having one or more sub-columns; each one of the one or more sub-columns having a predetermined position, the predetermined position being defined by one of predetermined sub-column edges or adjustable edges. The readout integrated circuit has a circuit comprising a number of detector boundary selection components, each one of the number of detector boundary selection components configured to select or adjust a detector boundary from at least one of a sub-column boundary or an adjustable boundary. The one or more processors are configured to perform the following for each segment of the detector array:

if a correction signal is received, activate selected ones of the number of detector boundary selection components, otherwise, use detector boundaries in a conventional configuration, and obtain, from each detector, a plurality of signals.

In one or more embodiments, the method of these teachings for correcting misalignment includes receiving, at a detector array, electromagnetic (EM) radiation from a target object. The detector array includes one or more detectors, the detectors organized into a plurality of segments, each segment having one or more rows of the detectors substantially perpendicular to a designed scan axis, each segment having one or more columns of detecting components substantially parallel to the designed scan axis, each column having one or more sub-columns. The detector array moves in a relative scan direction relative to the target object. A readout integrated circuit is operatively connected to the detector array, the readout integrated circuit including a number of detector boundary selection components, each one of the number of detector boundary selection components configured to select or adjust a detector boundary at a predetermined sub-column boundary or an adjustable sub-column boundary. The following operations are performed for each segment of the detector array: if there is misalignment at each segment, activate selected ones of the number of detector boundary selection components; the selected ones being selected to correct the misalignment by moving detector boundaries in order to correct misalignment, otherwise, using detector boundaries in a conventional configuration, and obtaining, from each segment of the detector array, a plurality of signals.

In one embodiment of these teachings, a given system that collects of plurality of detections of a target synthetically creates a higher resolution image of a target out of the plurality of detections when each of the plurality of detections is offset from the others by a known amount.

In one or more embodiments, the method of these teachings for improving image resolution includes (a) receiving, at a detector array, electromagnetic (EM) radiation from a target object. The detector array includes one or more detectors, the detectors organized into a plurality of segments, each segment having one or more rows of the detectors substantially perpendicular to a designed scan axis, each segment having one or more columns of detecting components substantially parallel to the designed scan axis, each column having one or more sub-columns. The detector array moves in a relative scan direction relative to the target object. A readout integrated circuit is operatively connected to the detector array, the readout integrated circuit including a number of detector boundary selection components, each one of the number of detector boundary selection components configured to select or adjust a detector boundary at a predetermined sub-column boundary or an adjustable sub-column boundary. (b) The following are performed for each segment of the detector array: if electromagnetic (EM) radiation is received from the target object in a first detection, use detector boundaries in a conventional configuration; otherwise, activate selected ones of the number of detector boundary selection components. (c) From each segment of the detector array, a plurality of signals is obtained. Steps (a) through (c) are repeated a predetermined number of times. The selected ones of the number of detector boundary selection components are selected to produce a predetermined number of overlapping pluralities of signals. The selected ones of the number of detector boundary selection components are also selected according to an image resolution improvement prescription.

A number of other embodiments are also disclosed.

For a better understanding of the present teachings, together with other and further objects thereof, reference is made to the accompanying drawings and detailed description and its scope will be pointed out in the appended claims.

BRIEF DESCRIPTION OF THE DRAWINGS

FIGS. 3a-3d show other embodiments of the boundary selection components as used in the system of these teachings;

DETAILED DESCRIPTION

The following detailed description presents the currently contemplated modes of carrying out these teachings. The description is not to be taken in a limiting sense, but is made merely for the purpose of illustrating the general principles of these teachings.

As used herein, the singular forms "a," "an," and "the" include the plural reference unless the context clearly dictates otherwise.

Systems and methods for adjusting detector position and size in detector arrays is disclosed herein below.

"Switch," as used herein, includes electronic switches such as switches including transistors, FETs and similar devices.

A "field manipulator," as used herein, is a boundary selection component, such as a grid and/or implant, operatively connected to a detector array in order to perform detector boundary selection or adjustment.

In one or more embodiments, the system of these teachings includes a detector array configured to receive electromagnetic (EM) radiation from a target object, the detector array having one or more detectors. The system also includes a readout integrated circuit and one or more processors. In the detector array, the detectors are organized into a plurality of segments, each segment having one or more rows of the detectors substantially perpendicular to a designed scan axis, each segment having a one or more columns of detecting components substantially parallel to the designed scan axis, each of the one or more columns having one or more sub-columns; each one of the one or more sub-columns having a predetermined position, the predetermined position being defined by one of predetermined sub-column edges or adjustable edges. The readout integrated circuit has a circuit comprising a number of detector boundary selection components, each one of the number of detector boundary selection components configured to select or adjust a detector boundary from least one of a predetermined sub-column boundary or adjustable sub-column boundary. The one or more processors are configured to perform the following for each segment of the detector array:

if a correction signal is received, activate selected ones of the number of detector boundary selection components, otherwise, use detector boundaries in a conventional configuration, and obtain, from each detector, a plurality of signals.

Figure 1A:
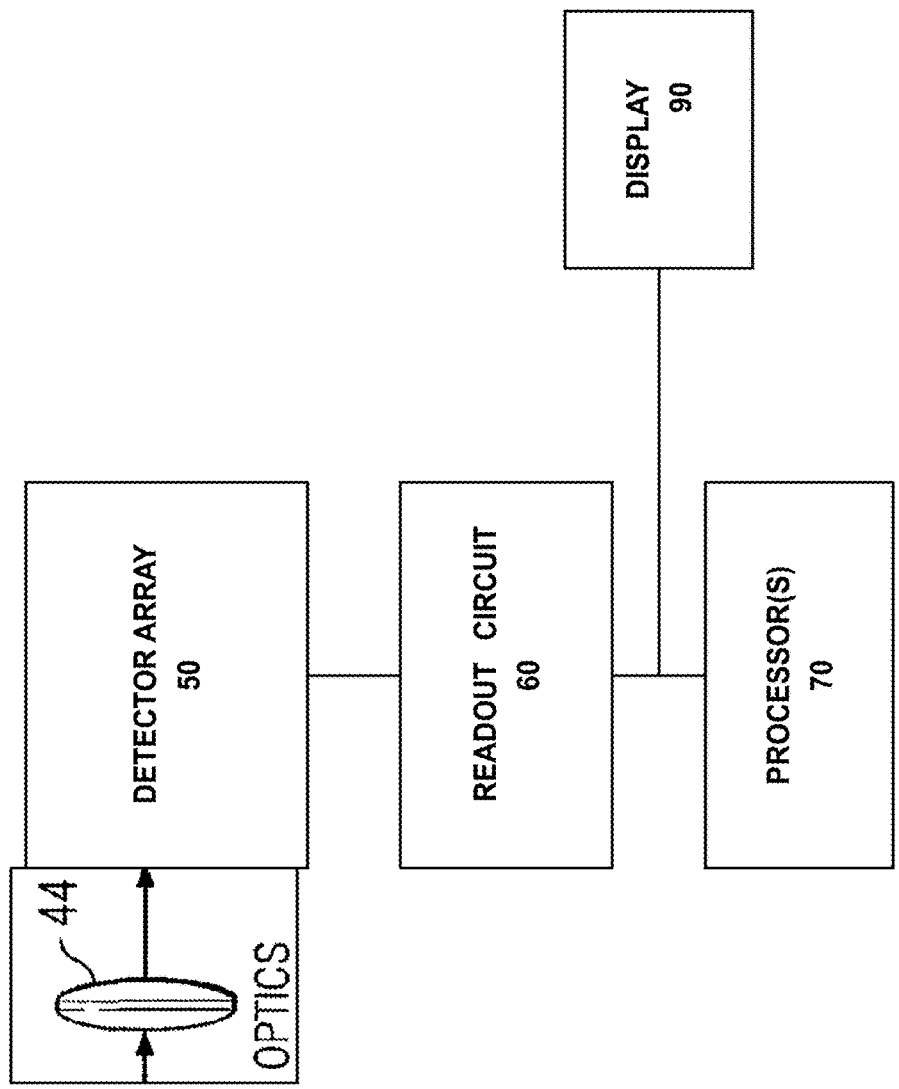
FIGS. 1a and 1b show embodiments of the system of these teachings.

One embodiment of the system of these teachings is shown in FIG. 1a. Referring to FIG. 1a, in the embodiment shown therein, electromagnetic radiation from a target object is imaged onto a detector array 50 by an optical subsystem 44. The system also includes a readout circuit 60 and one or more processors 70. (In one instance, the one or more processors 70 can be integrated into the readout circuit 60.) The readout circuit includes a number of detector boundary selection components, each one of the number of detector boundary selection components configured to select or adjust a detector boundary from least one of a sub-column boundary or an adjustable sub-column boundary. The one or more processors are configured to perform the following for each segment of the detector array:

if a correction signal is received, activate selected ones of the number of detector boundary selection components, otherwise, use detector boundaries in a conventional configuration, and obtain, from each detector, a plurality of signals. In one instance, the system also includes an output module 90 configured to display the resulting image generated from the image data.

Figure 1B:
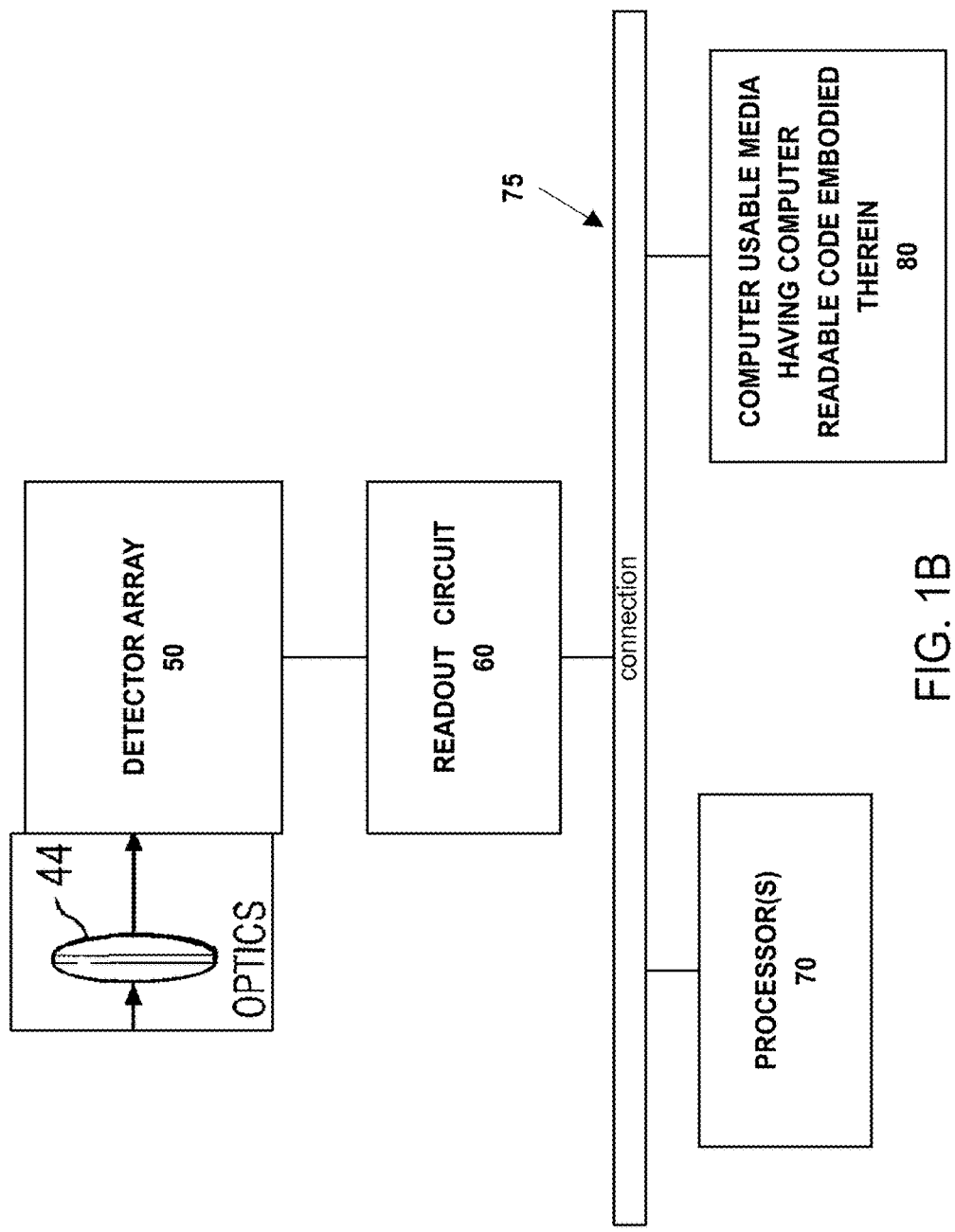

Another embodiment of the system of these teachings is shown in FIG. 1b. Referring to FIG. 1b, in the embodiment shown there in, the one or more processors 70 are configured to perform the above described actions by executing computer readable code embodied in a computer readable media

80. The computer readable media 80 is operatively connected to the one or more processors 70 by a connection component 75.

In one instance, the correction signal is received when there is misalignment at one or more segment. The one or more processors 70 are also configured to perform the following for each signal from the plurality of signals in order to yield a plurality of portions of a resulting image: obtain the scan data from said each signal, said each signal accumulating scan data of a portion of the target object; and generate image data from the scan data for a portion of the resulting image that corresponds to the portion of the target object.

Figure 2B:
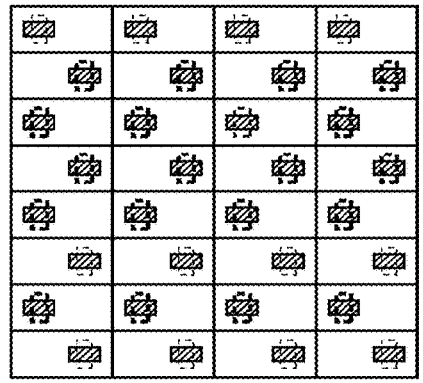
FIGS. 2a-2d show embodiments of the boundary selection components as used in the system of these teachings.
Figure 2C:
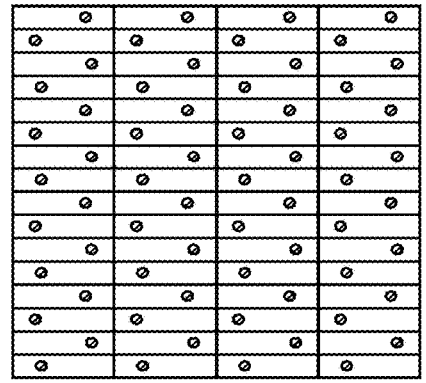
Figure 2A:
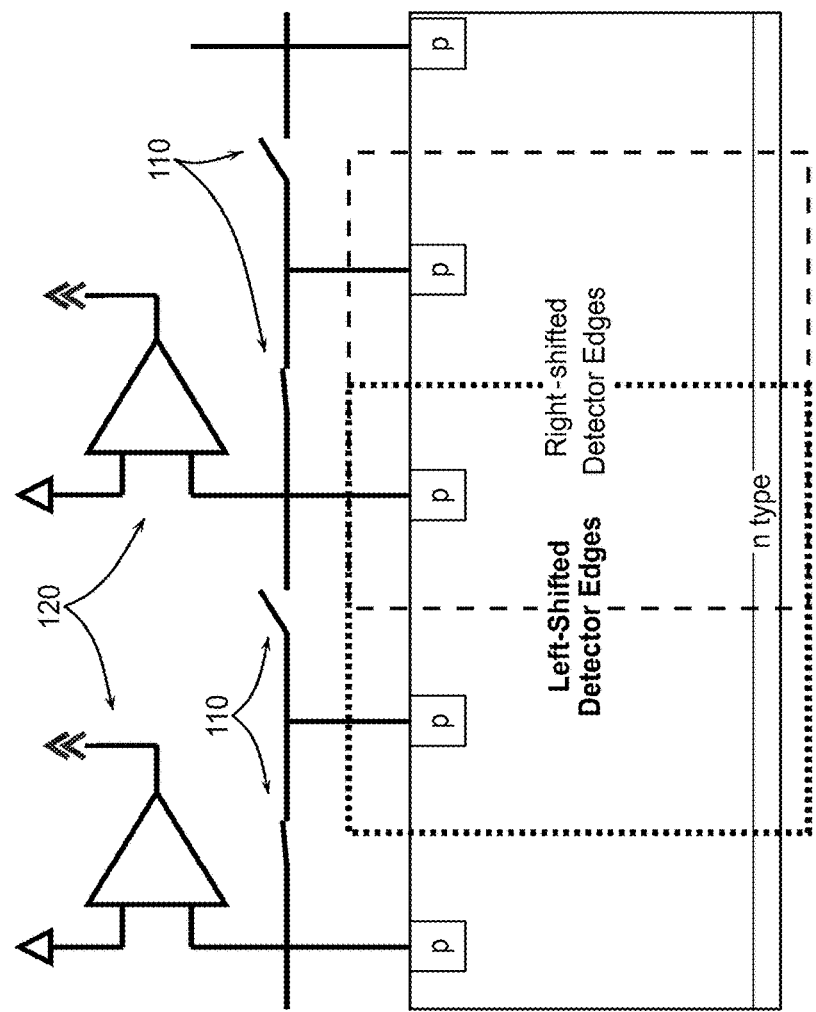

In one instance, each detector boundary selection component from the number of detector boundary selection components includes a switch. Embodiments of detector boundary selection components where each detector boundary selection component includes a switch are shown in FIGS. 2a-2d. Referring to FIG. 2a, in the embodiment shown there in, the detector pixels are divided into sub pixels (these pixels may represent columns and sub-columns in cross-section for the instance in which detector segments consist of a single column). An embodiment with two sub pixels is shown in FIG. 2b; an embodiment with 4 sub pixels is shown in FIG. 2c. The switches 110 in the readout circuit control collection by the individual receivers 120. In one embodiment, as shown in FIG. 2a, detector boundaries are moved by one of right shifting or left shifting. In one instance, as shown in FIG. 2a, detector size is substantially preserved.

Figure 2D:
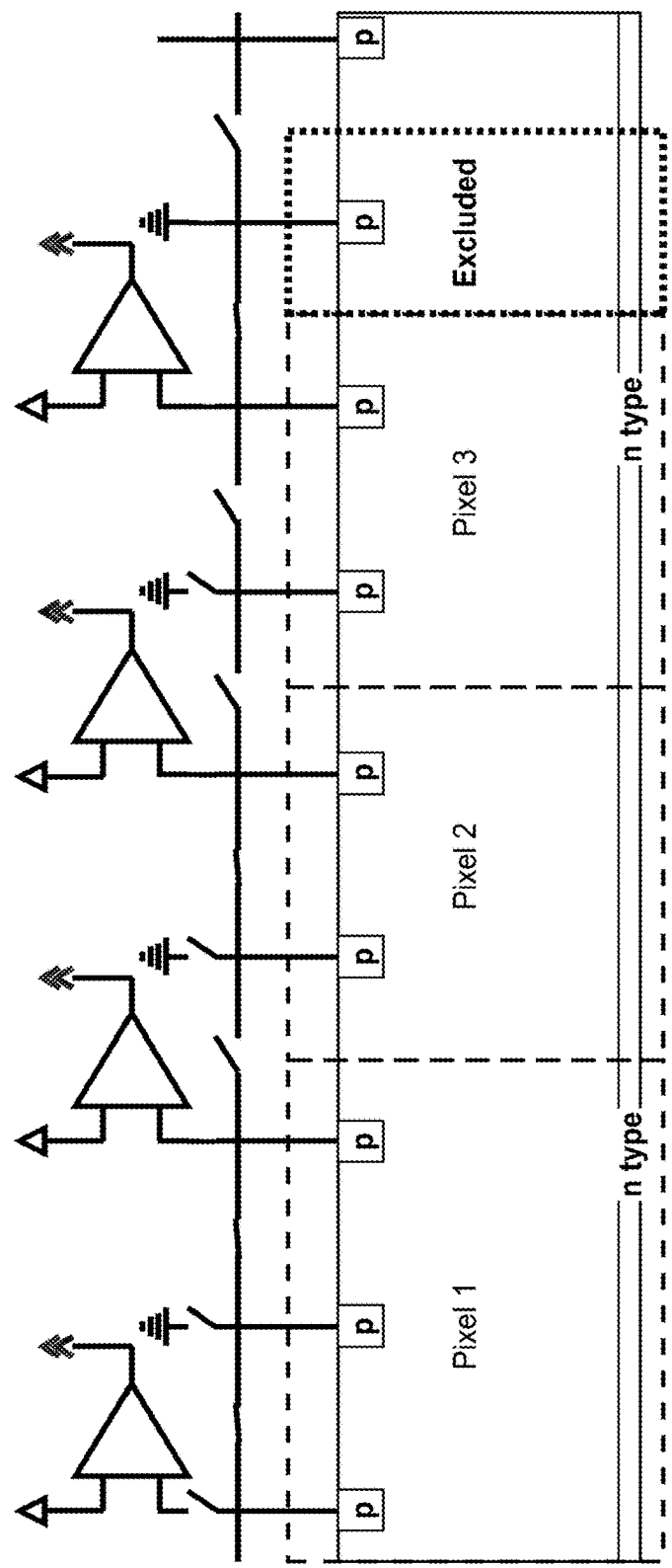

In one embodiment, shown in FIG. 2d, detector boundaries are moved and detector size is not required to be constant. In that embodiment, individual sub pixels can be excluded and individual receivers can be disconnected. When the correction signal is received when there is misalignment at one or more segment, that embodiment accommodates varying degrees of smear or misalignment across the sensor.

Figure 3A:
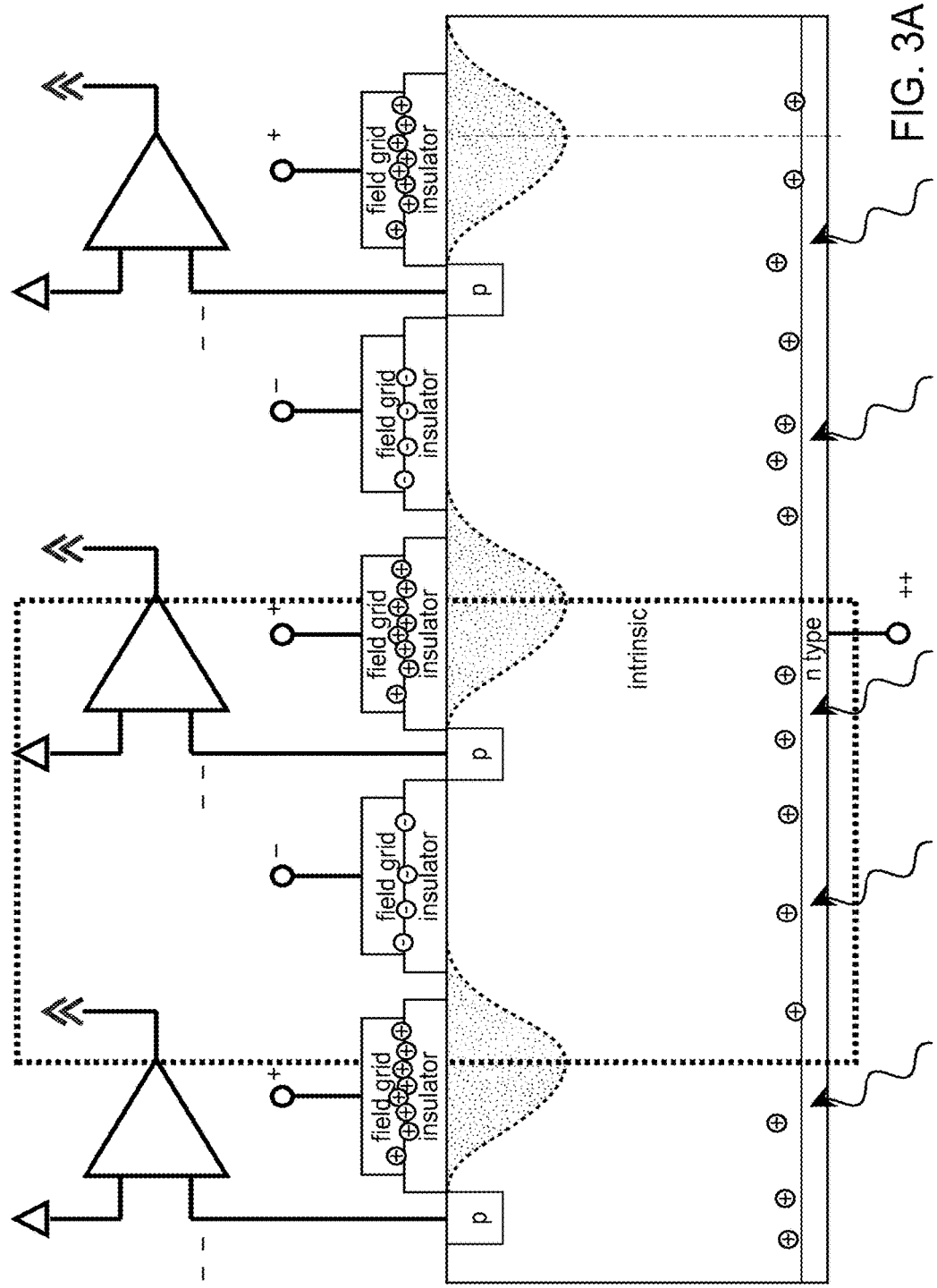
Figure 3B:
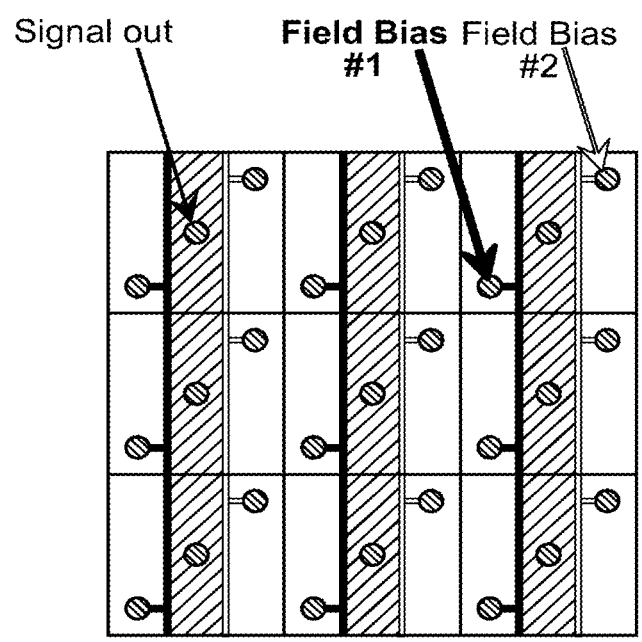

In another embodiment, shown in FIG. 3a, the detector pixel edges are defined by fields and the fields are exerted by two or more field manipulators (grids and/or implants) per detector pixel. Control of the fields can also fine-tune the pixel detector edges. Referring to FIG. 3a, in the embodiment shown therein, activating a field manipulator creates electric fields that sort carriers into the signal receivers and define the boundaries selected for each detector segment. FIG. 3b shows a top down view of the detector. (The component that activates the field manipulators are not shown but are conventional.) The signal out components are connected to the individual receivers. FIGS. 3c and 3d show another instance of an embodiment where the detector pixel edges are defined by fields. Referring to FIGS. 3c and 3d, in the embodiment shown there in, three field manipulators 1, 2, 3 are used.

In the embodiment shown in FIGS. 3a-3d, pixels of different size can be obtained and individual receivers can be disconnected to obtain larger pixel sizes.

In one or more embodiments, the method of these teachings for correcting misalignment includes receiving, at a detector array, electromagnetic (EM) radiation from a target object. The detector array includes one or more detectors, the detectors organized into a plurality of segments, each segment having one or more rows of the detectors substantially perpendicular to a designed scan axis, each segment having one or more columns of detecting components substantially parallel to the designed scan axis, each column having one or more sub-columns. The detector array moves in a relative scan direction relative to the target object. A readout integrated circuit is operatively connected to the detector array, the readout integrated circuit including a number of detector boundary selection components, each one of the number of detector boundary selection components configured to select or adjust a detector boundary at a predetermined sub-column boundary or an adjustable sub-column boundary. The following operations are performed for each segment of the detector array: if there is misalignment at a segment, activating selected ones of the number of detector boundary selection components; the selected ones being selected to correct the misalignment by moving detector boundaries in order to correct misalignment, otherwise, using detector boundaries in a conventional configuration, and obtaining, from each segment of the detector array, a plurality of signals.

Misalignment may result from a number of situations. For example, a failure in the production or use of a system might cause the system to fail to move a scanning subsystem in a relative scan direction that is parallel to the designed scan axis. As another example, a scanning system may use optics that distort radiation from a target object such that relative scan direction fails to be parallel to the designed scan axis. As another example, the target object may have a shape (such as a non-flat shape) that the scanning system cannot scan in a relative scan direction that is constantly parallel to the designed scan axis.

The misalignment present in a particular system may be determined in any suitable manner. For example, misalignment may be determined during calibration of the system. The Sensor system may then be configured to compensate for the misalignment. As another example, misalignment may be determined dynamically while the system is in use. A feedback system may detect the appearance of or changes in misalignment while the system is in use. A feedback system may notify the sensor system of the misalignment, which may then be configured to compensate for the misalignment.

Figure 4A:
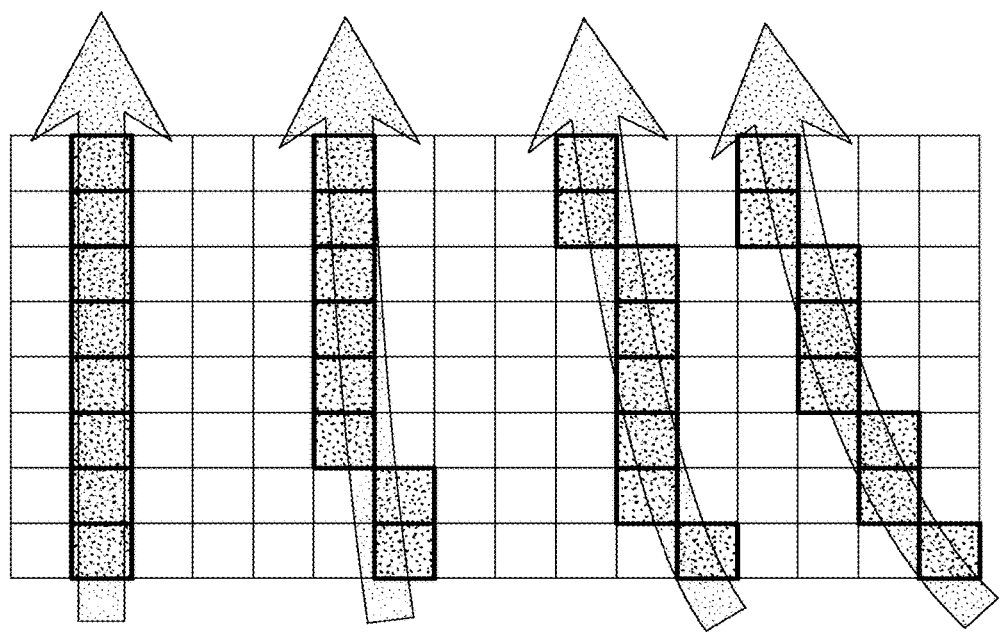
FIG. 4a illustrates a conventional method for correction of misalignment.

FIG. 4a shows the conventional correction of misalignment. The correction of misalignment shown in FIG. 4a is that described in U.S. Pat. No. 8,300,276, which is incorporated by reference here in its entirety and for all purposes.

Figure 4B:
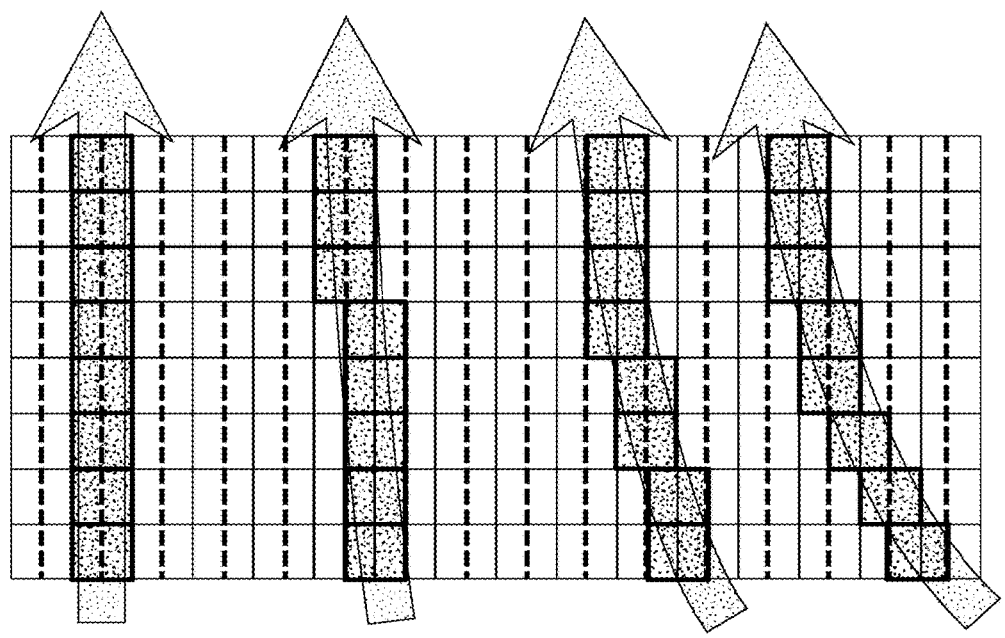
FIG. 4b illustrates one embodiment of the method of these teachings are for correction of misalignment.

FIG. 4b illustrates the correction of misalignment using one embodiment of the present teachings. In the embodiment shown in FIG. 4b, the boundaries (edges) of the detector pixels are changed from row to row in order to track the cross scan movement of the image elements as they are scanned across the detector array. Applying the method of these teachings, the cross scan misalignment (also referred to as cross scan smear) can be reduced to less than half a pixel. The reduction in misalignment results in images with better modulation transfer function. In applications, the reduction in misalignment results in reduced jitter requirements or reduce transmitted disturbance requirements for the system as a whole, or for pertinent subsystems.

In one instance, the embodiment of the method of these teachings for correcting misalignment also includes performing the following for each signal to yield a plurality of portions of a resulting image: obtaining the scan data from the each signal, each signal accumulating scan data of a portion of the target object; and generating image data from the scan data for a portion of the resulting image that corresponds to the portion of the target object.

In another instance, the number of sub-columns per column is n, and there is misalignment at each segment if a portion of the target object has moved substantially at least ½n of a column relative to the each column.

In one instance, each segment includes two or more rows of the detectors.

In one or more other embodiments, the method of these teachings for improving image resolution includes (a) receiving, at a detector array, electromagnetic (EM) radiation from a target object. The detector array includes one or more detectors, the detectors organized into a plurality of segments, each segment having one or more rows of the detectors substantially perpendicular to a designed scan axis, each segment having one or more columns of detecting components substantially parallel to the designed scan axis, each column having one or more sub-columns. The detector array moves in a relative scan direction relative to the target object. A readout integrated circuit is operatively connected to the detector array, the readout integrated circuit including a number of detector boundary selection components, each one of the number of detector boundary selection components configured to select or adjust a detector boundary at a predetermined sub-column boundary or an adjustable sub-column boundary.

(b) The following are performed for each segment of the detector array: if electromagnetic (EM) radiation is received from the target object in a first detection, use detector boundaries in a conventional configuration; otherwise, activate selected ones of the number of detector boundary selection components. (c) From each segment of the detector array, a plurality of signals is obtained. Steps (a) through (c) are repeated a predetermined number of times. The selected ones of the number of detector boundary selection components are selected to produce a predetermined number of overlapping pluralities of signals. The selected ones of the number of detector boundary selection components are also selected according to an image resolution improvement prescription and/or algorithm.

In one instance, each detector boundary selection component from the number of detector boundary selection components is a switch. In another instance, each detector boundary selection component from the number of detector boundary selection components comprises at least two field manipulators (grids and/or implants) operatively attached to the detector array.

In one instance, detector (pixel) boundaries are moved by one of right shifting or left shifting and detector (pixel) size is substantially preserved. In another instance, detector (pixel) boundaries are moved and detector (pixel) size is not required to be constant.

Figure 5:
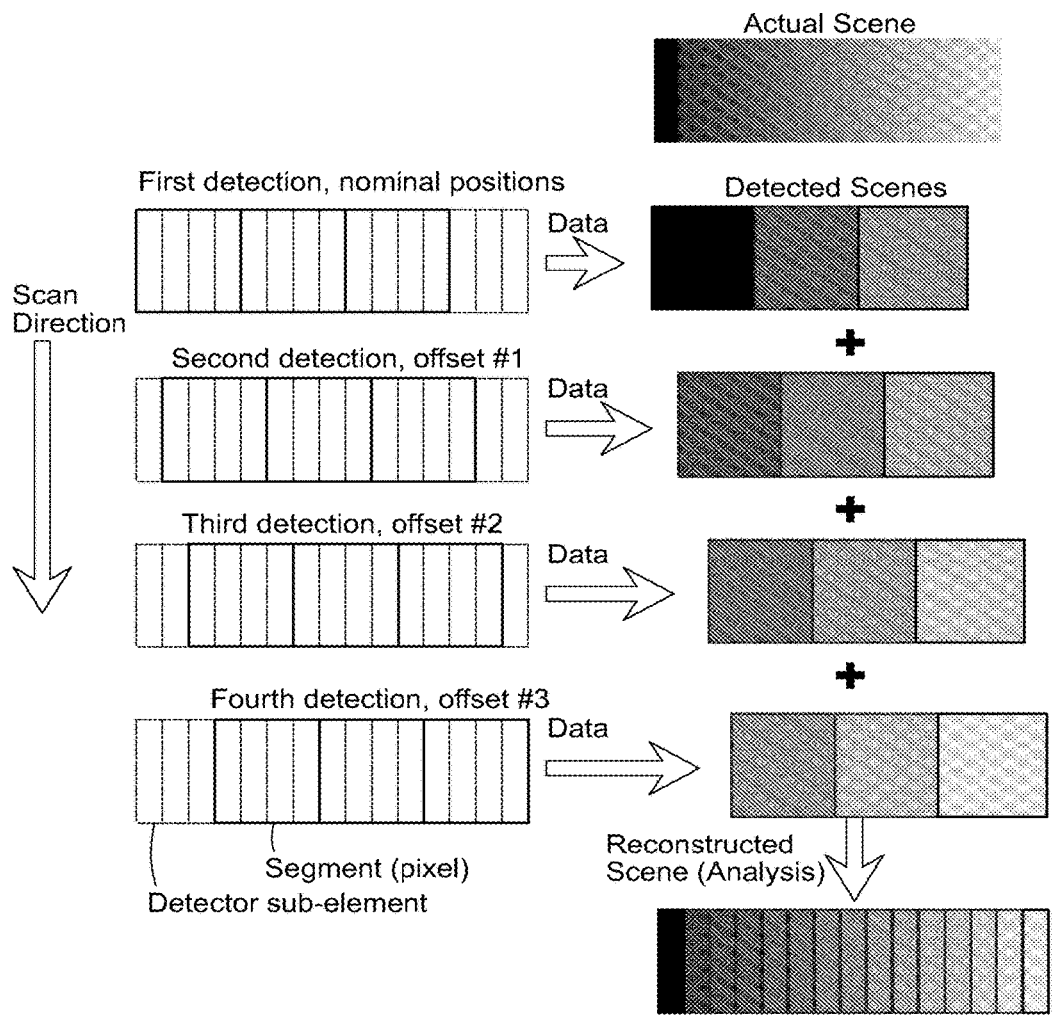
FIG. 5 illustrates one embodiment of the method of these teachings for improving image resolution.

FIG. 5 shows one embodiment of the method of these teachings for improving image resolution. Referring to FIG. 5, in the embodiment shown therein, in the first detection, the conventional pixel positions are used. In the subsequent detections, the detector boundary selection components are activated in order to obtain pixel positions such that the group of pixels is offset from the previous detection. Although in FIG. 5, the pixels are shown as being all of one size, this embodiment is not limited to instances where the pixel size is required to be substantially constant.

The following is a disclosure by way of example of a device configured to execute functions (hereinafter referred to as computing device) which may be used with the presently disclosed subject matter. The description of the various components of a computing device is not intended to represent any particular architecture or manner of interconnecting the components. Other systems that have fewer or more components may also be used with the disclosed subject matter. A communication device may constitute a form of a computing device and may at least include a computing device. The computing device may include an interconnect (e.g., bus and system core logic), which can interconnect such components of a computing device to a data processing device, such as a processor(s) or microprocessor(s), or other form of partly or completely programmable or pre-programmed device, e.g., hard wired and or application specific integrated circuit (ASIC), customized logic circuitry, such as a controller or microcontroller, a digital signal processor, or any other form of device that can fetch instructions, operate on pre-loaded/pre-programmed instructions, and/or follow instructions found in hard-wired or customized circuitry to carry out logic operations that, together, perform steps of and whole processes and functionalities as described in the present disclosure.

In this description, various functions, functionalities and/or operations may be described as being performed by or caused by software program code to simplify description. However, those skilled in the art will recognize what is meant by such expressions is that the functions result from execution of the program code/instructions by a computing device as described above, e.g., including a processor, such as a microprocessor, microcontroller, logic circuit or the like. Alternatively, or in combination, the functions and operations can be implemented using special purpose circuitry, with or without software instructions, such as using ASIC or Field-Programmable Gate Array (FPGA), which may be programmable, partly programmable or hard-wired. The ASIC logic may be such as gate arrays or standard cells, or the like, implementing customized logic by metalization(s) interconnects of the base gate array ASIC architecture or selecting and providing metalization(s) interconnects between standard cell functional blocks included in a manufacturer's library of functional blocks, etc. Embodiments can thus be implemented using hard-wired circuitry without program software code/instructions, or in combination with circuitry using programmed software code/instructions.

Thus, the techniques are limited neither to any specific combination of hardware circuitry and software, nor to any particular tangible source for the instructions executed by the data processor(s) within the computing device. While some embodiments can be implemented in fully functioning computers and computer systems, various embodiments are capable of being distributed as a computing device including, e.g., a variety of forms and capable of being applied regardless of the particular type of machine or tangible computer-readable media used to actually effect the performance of the functions and operations and/or the distribution of the performance of the functions, functionalities and/or operations.

The interconnect may connect the data processing device to define logic circuitry including memory. The interconnect may be internal to the data processing device, such as coupling a microprocessor to on-board cache memory or external (to the microprocessor) memory such as main memory, or a disk drive external to the computing device, such as a remote memory, a disc farm or other mass storage device, etc.

The memory may include any tangible computer-readable media, which may include but are not limited to recordable and non-recordable type media such as volatile and non-volatile memory devices, such as volatile RAM (Random Access Memory), typically implemented as dynamic RAM (DRAM) which requires power continually in order to refresh or maintain the data in the memory, and non-volatile ROM (Read Only Memory), and other types of non-volatile memory, such as a hard drive, flash memory, detachable memory stick, etc. Non-volatile memory typically may include a magnetic hard drive, a magnetic optical drive, or an optical drive (e.g., a DVD RAM, a CD ROM, a DVD or a CD), or other type of memory system which maintains data even after power is removed from the system.

At least some aspects of the disclosed subject matter can be embodied, at least in part, utilizing programmed software code/instructions. That is, the functions, functionalities and/or operations techniques may be carried out in a computing device or other data processing system in response to its processor, such as a microprocessor, executing sequences of instructions contained in a memory, such as ROM, volatile RAM, non-volatile memory, cache or a remote storage device. In general, the routines executed to implement the embodiments of the disclosed subject matter may be implemented as part of an operating system or a specific application, component, program, object, module or sequence of instructions usually referred to as "computer programs," or "software." The computer programs typically comprise instructions stored at various times in various tangible memory and storage devices in a computing device, such as in cache memory, main memory, internal or external disk drives, and other remote storage devices, such as a disc farm, and when read and executed by a processor(s) in the computing device, cause the computing device to perform a method(s), e.g., process and operation steps to execute an element(s) as part of some aspect(s) of the method(s) of the disclosed subject matter.

A tangible machine readable medium can be used to store software and data that, when executed by a computing device, causes the computing device to perform a method(s) as may be recited in one or more accompanying claims defining the disclosed subject matter. The tangible machine readable medium may include storage of the executable software program code/instructions and data in various tangible locations, including for example ROM, volatile RAM, non-volatile memory and/or cache. Portions of this program software code/instructions and/or data may be stored in any one of these storage devices. Further, the program software code/instructions can be obtained from remote storage, including, e.g., through centralized servers or peer-to-peer networks and the like. Different portions of the software program code/instructions and data can be obtained at different times and in different communication sessions or in a same communication session.

The software program code/instructions and data can be obtained in their entirety prior to the execution of a respective software application by the computing device. Alternatively, portions of the software program code/instructions and data can be obtained dynamically, e.g., just in time, when needed for execution. Alternatively, some combination of these ways of obtaining the software program code/instructions and data may occur, e.g., for different applications, components, programs, objects, modules, routines or other sequences of instructions or organization of sequences of instructions, by way of example. Thus, it is not required that the data and instructions be on a single machine readable medium in entirety at any particular instance of time.

In general, a tangible machine readable medium includes any tangible mechanism that provides (i.e., stores) information in a form accessible by a machine (i.e., a computing device, which may be included, e.g., in a communication device, a network device, a personal digital assistant, a mobile communication device, whether or not able to download and run applications from the communication network, such as the Internet, e.g., an iPhone, Blackberry, Droid or the like, a manufacturing tool, or any other device including a computing device, comprising one or more data processors, etc.

For the purposes of describing and defining the present teachings, it is noted that the term "substantially" is utilized herein to represent the inherent degree of uncertainty that may be attributed to any quantitative comparison, value, measurement, or other representation.

The term "substantially" is also utilized herein to represent the degree by which a quantitative representation may vary from a stated reference without resulting in a change in the basic function of the subject matter at issue.

Although the invention has been described with respect to various embodiments, it should be realized these teachings are also capable of a wide variety of further and other embodiments within the spirit and scope of the appended claims.

What is claimed is:

1. A method for correcting misalignment, the method comprising:
   receiving, at a detector array, electromagnetic (EM) radiation from a target object, the detector array comprising one or more detectors, each detector organized into a plurality of segments, each segment comprising one or more rows of the detector substantially perpendicular to a designed scan axis, each segment comprising one or more columns of detecting components substantially parallel to the designed scan axis, each column comprising one or more sub-columns; the detector array moving in a relative scan direction relative to the target object; a readout circuit being operatively connected to the detector array, the readout circuit comprising a number of detector boundary selection components, each one of the number of detector boundary selection components configured to select or adjust a detector boundary at one sub-column boundary or adjustable sub-column boundary; and
   performing the following for each segment of the detector array:
      if there is misalignment at a segment, activating selected ones of the number of detector boundary selection components; the selected ones being selected to correct the misalignment by moving detector boundaries in order to correct misalignment; otherwise, using detector boundaries in a conventional configuration; and
      obtaining, from said each segment of the detector array, a plurality of signals.

2. The method of claim 1, further comprising performing the following for each signal to yield a plurality of portions of a resulting image: obtaining scan data from the each signal, the each signal accumulating the scan data of a portion of the target object; and generating image data from the scan data for a portion of the resulting image that corresponds to the portion of the target object.

3. The method of claim 1, wherein a number of the one or more sub-columns per column is n; and wherein there is misalignment at the each segment if a portion of the target object has moved substantially at least $\frac{1}{2}n$ of a column relative to the each column.

4. The method of claim 1, wherein each detector boundary selection component from the number of detector boundary selection components is a switch.

5. The method of claim 1, wherein each detector boundary selection component from the number of detector boundary selection components comprises at least two field manipulators operatively attached to the detector array.

6. The method of claim 1, wherein detector boundaries are moved by one of right shifting or left shifting; and wherein detector size is substantially preserved.

7. The method of claim 1, wherein detector boundaries are moved and wherein detector size is not required to be constant.

8. The method of claim 1, wherein each segment comprises two or more rows of the detector.

\* \* \* \* \*